United States Patent [19]

Johnson et al.

[11] 4,356,150
[45] Oct. 26, 1982

[54] HUMIDITY SENSOR WITH ELECTRICAL REJECTION OF CONTAMINANTS

[75] Inventors: Robert G. Johnson, Minnetonka; Thomas E. Hendrickson, Wayazata, both of Minn.

[73] Assignee: Honeywell Inc., Minneapolis, Minn.

[21] Appl. No.: 263,945

[22] Filed: May 15, 1981

[51] Int. Cl.³ .................. G01R 27/02; H01L 7/00
[52] U.S. Cl. ................................ 422/98; 23/232 E; 73/336.5; 427/103; 338/35
[58] Field of Search ............... 422/98; 23/232 E; 338/35; 73/73, 336.5; 427/102, 103, 79, 80

[56] References Cited

U.S. PATENT DOCUMENTS

| | | |
|---|---|---|
| 3,864,659 | 2/1975 | Furuuchi et al. ............ 422/98 X |
| 3,961,301 | 6/1976 | Fraioli . |
| 4,015,230 | 3/1977 | Nitta et al. ................. 422/98 X |
| 4,080,564 | 3/1978 | Nitta et al. . |
| 4,143,177 | 3/1979 | Kovac et al. ............... 338/35 X |
| 4,203,087 | 5/1980 | Kovac et al. ............... 338/35 |
| 4,280,115 | 7/1981 | Farrington .................. 422/98 X |
| 4,321,577 | 3/1982 | Carlson ...................... 422/98 X |

Primary Examiner—Ronald E. Serwin
Attorney, Agent, or Firm—Omund R. Dahle

[57] ABSTRACT

A conductivity type thin film humidity sensor on a silicon chip which sensor includes structure which electrically shields the sensing area from highly dissociative contaminants.

22 Claims, 1 Drawing Figure

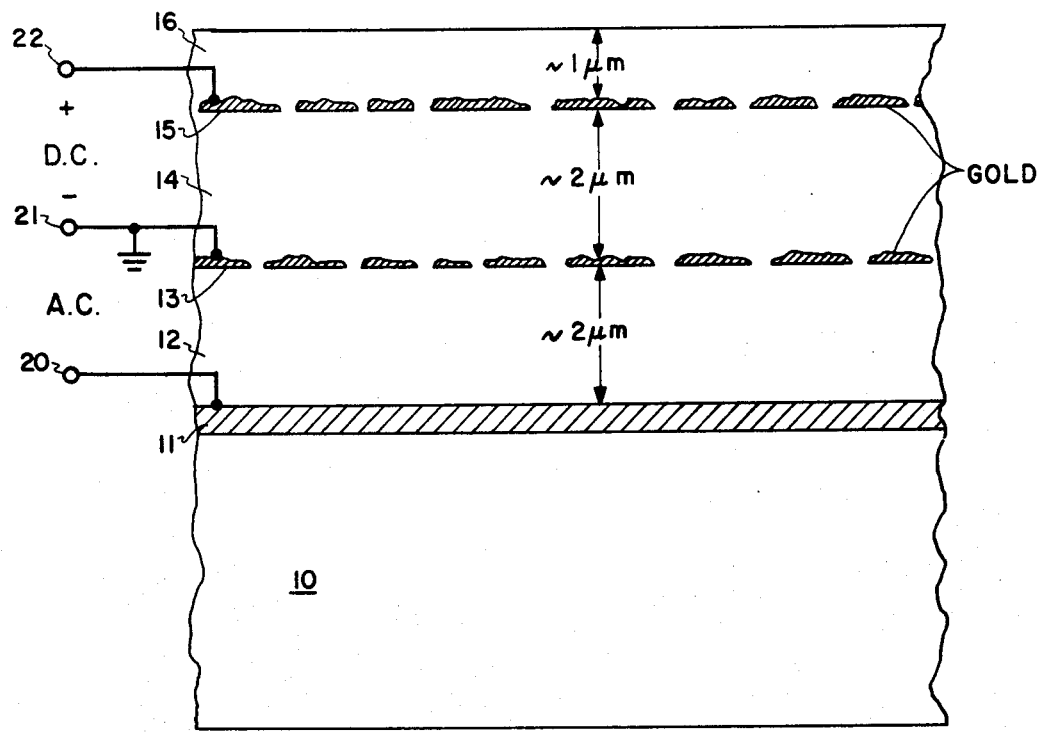

HUMIDITY SENSOR WITH ELECTRICAL REJECTION OF CONTAMINANTS

BACKGROUND AND SUMMARY OF THE INVENTION

The field of the invention is that of humidity sensors which are compatible with silicon technology and include structure which electrically shields the sensing area from highly dissociative contaminants. There are other known types of humidity sensors having contaminant protection devices such as shown in U.S. Pat. Nos. 3,961,301 and 4,080,564.

The present invention relates to a porous $SiO_2$ or $FE_2O_3$ conductivity type humidity sensor. It has electrode layers incorporated in the sensor structure which are energized to prevent contaminants such as $H_2SO_4$, $HNO_3$, NaOH, KOH, NaCl and $CuCl_2$ from reaching the active area of the sensor structure. Applied bias voltages minimize baseline drift by preventing contaminants from entering the sensing region.

BRIEF DESCRIPTION OF THE DRAWING

The single FIGURE of the drawing is a cross sectional view of the humidity sensor according to the invention.

DESCRIPTION

The present invention is directed to a humidity sensor structure which minimizes the effect of air borne contaminants such as sulfates, nitrates and other contaminants on the stability of the sensor. Referring now the FIGURE there is shown as a supporting substrate for the sensor a silicon chip 10 which has sputtered thereon about 1000 A° of Ni-Fe to form one electrode 11 of the sensor. Over the electrode is sputtered porous $SiO_2$ or $Fe_2O_3$ in a layer 12 about 2 $\mu$m thick. Then a porous electrode 13 of "clumped" gold or platinum consisting of interconnected clumps having an average thickness of about 100 A° is deposited by sputtering. Elements 11, 12 and 13 form the basic conductivity-type sensor. Sputtering a second portion of porous $SiO_2$ or $Fe_2O_3$ continues at 14 for a thickness about the same as layer 12 or about 2 $\mu$m. A second porous electrode 15 like electrode 13 is then sputtered. Finally a porous overlayer 16 of $SiO_2$ or $Fe_2O_3$ is sputtered comparable to layers 12 and 14. Electrical contact terminals 20, 21 and 22 make contact with electrodes 11, 13 and 15 respectively. These may be integrated on the silicon chip.

In the sputtering of the porous $SiO_2$ or $Fe_2O_3$ layers described above, these layers are preferably originally sputtered down as an alkali glass, or as as a $SiO_2$-$B_2O_3$ mixture, or as a $Fe_2O_3$-$B_2O_3$ mixture. When the sputtering operations are completed the structure may be annealed to permit the proper amount of phase separation. The structure is then boiled in water to leach out the interconnected phase regions containing the alkali oxides, or the $B_2O_3$ molecules leaving the porous $SiO_2$ or $Fe_2O_3$ structure. Variations of the mixture of the sputtering oxides and also the conditions of the anneal are effective in adjusting to a preferred value the final porosity of the finished sensors. In use, atmospheric water concentrations are sensed when the water vapor in the ambient air equilibrates with adsorbed water on the internal surfaces of the porous structure by surface diffusion through the pores, and thus alters the AC conductivity of the lower layer 12.

In certain applications it may be desirable to modify the completed sensor by an additional step, and convert the porous $SiO_2$ to porous silicon nitride ($Si_3N_4$). An advantage of a nitride is that the silicon nitride material, per se, is not permeated with or penetrated by water vapor to the extent that the silicon oxide material is. The conversion is accomplished by heating the completed silicon oxide structure in an ammonia ($NH_3$) atmosphere at about 800–900 C. so that a reaction takes place in which the nitrogen replaces the oxygen thereby converting the $SiO_2$ to $Si_3N_4$. One reason for converting is that under certain operating conditions there may be a tendency for an undesirable limited hydrolyzing to occur with the $SiO_2$ which will not occur with the $Si_3N_4$.

In operation, an AC potential is applied to the sensor terminals 20 and 21 so that the proper sensing level is applied across sensing element 12 and the conductivity of the circuit is measured. The humidity diffuses through the pores of layers 16 and 14 and into sensing layer 12 where changes in humidity result in changes in conductivity measured. The layers of porous $SiO_2$ 16 and 14 together with electrodes 15 and 13 may be referred to as contaminant capture layers. A DC potential is applied across terminals 21 and 22 and the electric field capture layer repels the ionized atoms of the strong electrolytes which ionize easily, and prevent them from penetrating to the sensing layer 12. The polarity of the DC bias voltage on the conductive layer 22 prevents the negative ions of the contaminants (i.e. $SO_4$, $NO_3$, etc.) from diffusing across to the sensing region 12. While two porous gold electrode layers 13 and 15 are shown in the drawing, a modification would include another porous electrode layer spaced above layer 15 and electrically biased with the opposite polarity where positive contaminant ions prove to be a problem. As examples, such airborne contaminants which may diffuse into the sensor and cause erroneous readings include acids such as $H_2SO_4$ and $HNO_3$, such gases as NaOH and KOH, and such salts as NaCl and CuCl. The important result of the capture layer as shown in the FIGURE is that the negative ions of highly dissociative compounds will not get to the sensing layer. The second layer and electrode spaced above 15 and oppositely biased prevent the corresponding positive ions from reaching the sensing layer. The second layer and electrode are directed particularly toward preventing positive ions other than hydrogen ions from reaching the sensing region. Hydrogen ions that might tend to collect near a negative electrode would combine to form $H_2$ and thus would diffuse out of the structure harmlessly as a gas. Other positive ions would not diffuse out as a gas.

The embodiments of the invention in which an exclusive property or right is claimed are defined as follows:

1. A thin film humidity sensor on a substrate comprising:
   a first humidity sensing section including;
      a metallic conductive thin film deposited on a substrate;
      a first thin film porous layer, selected from a group consisting of oxides and a nitride, deposited over said metallic film;
      a first thin film porous conductive layer over said porous layer, said metallic film and said first conductive layer being adapted to be connected to an AC source for energizing said humidity sensing section;

a second contaminant capture section overlaying said first sensing section including;
  a second thin film porous layer like said first thin film porous layer;
  a second thin film porous conductive layer over said second porous layer;
  and for mechanical protection, a third thin film porous layer over said second conductive layer, the humidity thus having to diffuse through the porous layers of said contaminant capture section to enter said humidity sensing section, and said second conductive layer being adapted to be connected to a DC source to electrically bias said contaminant capture section so that specific ionic contaminants are prevented from diffusing across to the sensing region.

2. The sensor according to claim 1 wherein the oxides are selected from a group consisting of $SiO_2$ and $Fe_2O_3$.

3. The sensor according to claim 2 wherein the porous oxide layers are $SiO_2$.

4. The sensor according to claim 2 wherein the porous oxide layers are $Fe_2O_3$.

5. The sensor according to claim 1 wherein the porous nitride layer is silicon nitride.

6. The sensor according to claim 1 wherein the first and second porous conductive layers are of gold.

7. The sensor according to claim 1 wherein the first and second porous conductive layers are of platinum.

8. The sensor according to claim 1 wherein the porous conductive layers are about 100 A° in thickness.

9. The sensor according to claim 1 wherein the first and second porous layers are about 2 $\mu$m in thickness.

10. A thin film humidity sensor on a substrate comprising:
  a first humidity sensing section including;
    a metallic conductive thin film deposited on a substrate;
    a first thin film layer of a porous oxide, selected from a group consisting of $SiO_2$ and $Fe_2O_3$ deposited over said metallic film;
    a first thin film porous conductive layer over said oxide layer, said metallic film and said first conductive layer being adapted to be connected to an AC source for energizing said humidity sensing section;
  a second contaminant capture section overlaying said first sensing section including;
    a second thin film layer of the porous oxide;
    a second thin film porous conductive layer over said second oxide layer;
    and for mechanical protection, a third thin film layer of the porous oxide over said second conductive layer, the humidity thus having to diffuse through the porous layers of said contaminant capture section to enter said humidity sensing section, and said second conductive layer being adapted to be connected to a DC source to electrically bias said contaminant capture section so that specific ionic contaminants are prevented from diffusing across to the sensing region.

11. The sensor according to claim 10 wherein the porous oxide layers are $SiO_2$.

12. The sensor according to claim 10 wherein the porous oxide layers are $Fe_2O_3$.

13. The sensor according to claim 10 wherein the first and second layers of porous oxide are about 2 $\mu$m in thickness.

14. A layered thin film humidity sensor comprising in order:
  an electrically conductive layer deposited on a substrate;
  a first thin film porous layer selected from a group consisting of $SiO_2$, $Fe_2O_3$, and $Si_3N_4$ deposited over said conductive layer;
  a first thin film porous electrically conductive layer over said first porous layer, said first three layers forming the basic humidity sensor;
  a second thin film porous layer deposited over said porous conductive layer;
  a second thin film porous electrically conductive layer over said second porous layer; and
  a third thin film porous layer deposited over said second porous conductive layer, said second three layers comprising a contaminant capture overlay of said basic sensor.

15. The sensor according to claim 14 wherein the first, second and third thin film porous layers are of the nitride $Si_3N_4$.

16. The sensor according to claim 14 wherein the first, second and third thin film porous layers are of the oxide $SiO_2$.

17. The sensor according to claim 14 wherein the first, second and third thin film porous layers are of the oxide $Fe_2O_3$.

18. A method of fabricating a thin film humidity sensor on a substrate comprising the steps of:
  depositing an electrically conductive film on a portion of a substrate;
  depositing a thin film layer of a porous oxide over the conductive film;
  depositing a very thin porous electrically conductive layer over said oxide layer;
  depositing a second thin film layer of the porous oxide over the thin porous conductive layer;
  depositing a second very thin porous electrically conductive layer over the second oxide layer;
  depositing a third thin film layer of the porous oxide over the second conductive layer.

19. A method of fabricating a thin film humidity sensor on a substrate comprising the steps of:
  depositing a conductive metallic film on a portion of a substrate;
  depositing a layer of oxide selected from a group consisting of a $SiO_2$-$B_2O_3$ mixture and a $Fe_2O_3$-$B_2O_3$ mixture over the metallic film;
  depositing a very thin porous conductive layer over the oxide layer;
  depositing a second layer of the oxide mixture over the porous conductive layer;
  depositing a second very thin porous conductive layer over the second oxide layer;
  depositing a third layer of the oxide mixture over the second porous conductive layer; and,
  leaching out said $B_2O_3$ from said layers in hot water to increase the porosity of said oxide layers.

20. The method according to claims 18 or 19 and further comprising the final step of:
  converting to a nitride the porous oxide layers by heating the sensor to about 800°–900° C. in an ammonia atmosphere.

21. The method according to claims 18 or 19 in which said oxide layers and said conductive layers are deposited by sputtering.

22. A thin film humidity sensor on a substrate according to claim 1 and further comprising:
  means for applying an AC source across said metallic film and said first thin film porous conductive layer; and,
  means for applying a DC source to said second thin film porous conductive layer to electrically bias said layer so that contaminants are prevented from diffusing to the sensing region.

* * * * *

UNITED STATES PATENT OFFICE
CERTIFICATE OF CORRECTION

PATENT NO. : 4,356,150
DATED : October 26, 1982
INVENTOR(S) : Robert G. Johnson et al It is certified that error appears in the above-identified patent and that said Letters Patent are hereby corrected as shown below:

Claim 6, line 1, after "claim 1" insert --or 10--.

Claim 7, line 1, after "claim 1" insert --or 10--.

Claim 8, line 1, after "claim 1" insert --or 10--.

Signed and Sealed this

Fifteenth Day of February 1983

[SEAL]

Attest:

GERALD J. MOSSINGHOFF

Attesting Officer     Commissioner of Patents and Trademarks